Figure 1:
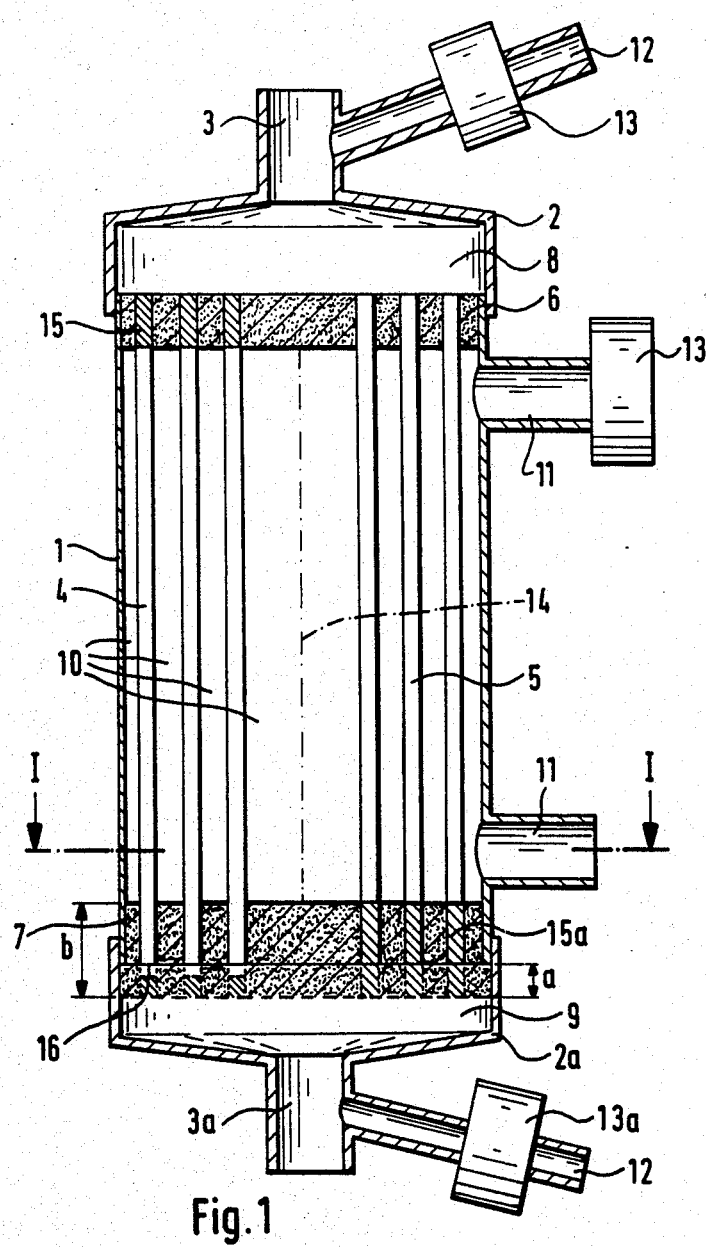

United States Patent [19]

Mathieu

[11] Patent Number: 4,784,768
[45] Date of Patent: Nov. 15, 1988

[54] CAPILLARY FILTER ARRANGEMENT FOR STERILIZATION OF LIQUID MEDIA

[75] Inventor: Bernd Mathieu, Spiesen-Elversberg, Fed. Rep. of Germany

[73] Assignee: Fresenius AG, Bad Homburg, Fed. Rep. of Germany

[21] Appl. No.: 169,815

[22] Filed: Mar. 18, 1988

[30] Foreign Application Priority Data

Mar. 21, 1987 [DE] Fed. Rep. of Germany ....... 3709432

[51] Int. Cl.$^4$ ............................................. B01D 13/00
[52] U.S. Cl. ............................. 210/321.8; 210/321.9; 210/323.2; 210/336
[58] Field of Search ..................... 210/323.2, 335, 336, 210/321.9, 321.8, 321.89; 264/41, 45.1, 45.2, 45.8

[56] References Cited

U.S. PATENT DOCUMENTS 4,000,072 12/1976 Sato et al. ..................... 210/321.8 X
4,451,396 5/1984 Sekino et al. ..................... 210/321.9

Primary Examiner—Frank Spear
Attorney, Agent, or Firm—Parmelee, Bollinger & Bramblett

[57] ABSTRACT

Capillary filter arrangement for the sterilization of liquid media comprising two semipermeable capillary fibre bundles (4, 5) which are in flow connection and which are arranged adjacent each other in a single housing (1). The opposite openings of the housing (1) are each sealed by an end cap (2; 2a) which comprises at least one connecting opening (3; 3a) for introduction or removal of the medium respectively. The housing (1) comprises at its ends a cast layer (6; 7) in which the ends of the capillary fibre bundles (4; 5) are received, a distributing space (8; 9) being formed between the end cap (2; 2a) and cast layer (6; 7) and a primary filtrate chamber (10) being formed between the cast layer (6; 7). The ends of the first capillary fibre bundle (4) are sealed with respect to the first distributing chamber (8) and the ends of the second capillary fibre bundle (5) are sealed with respect to the second distributing chamber (9) so that the entire internal lumen of the first and second capillary fibre bundle (4; 5) respectively is in flow connection only with the second and first distributing chamber (9; 8) respectively.

14 Claims, 2 Drawing Sheets

CAPILLARY FILTER ARRANGEMENT FOR STERILIZATION OF LIQUID MEDIA

The invention relates to a capillary filter arrangement for sterilization of liquid media having at least two semipermeable capillary fibre bundles which are in flow connection.

The filtration of media, in particular medical fluids for sterilization and/or removing pyrogens is applied at present in the preparation of substitution solutions in a dialysis ward.

DE-OS No. 3,444,671 describes a hemodifiltration apparatus having a dialyzer which is divided by a membrane into two chambers, the first chamber being connected into a dialysis solution path and the second chamber into a blood path.

The dialysis solution path comprises a supply conduit which extends from a means for preparing the dialysis solution to the dialyzer and into which a first balancing chamber is connected and a discharge conduit which extends from the dialyzer to the drain and into which a second balance chamber is connected. Furthermore, this apparatus comprises a pump for conveying the dialysis solution in the closed dialysis solution system and an ultrafiltration means provided between the balancing chmbers in the dialysis solution path, and also a connecting conduit which branches off the supply conduit between the first balance chamber and the dialyzer and which is connected to the blood path and into which at least one sterile filter and a pump are connected.

Trans. Am. Soc. Artif. Organ (ASAIO), 1978, page 465 to 467, discloses an on-line preparation of a sterile and pyrogen-free substituate which is prepared by employing the usual proportioning unit for preparing the usual dialysis solution. A concentrate is mixed with water in a ratio of 1:34. The dialysis solution thus made is subsequently degasified and heated and thereafter supplied to two ultrafilters which are connected in series. At the end of the second filter a sterile pyrogen-free substituate is obtained which then leads to the blood path.

EP-OS No. 42,939 discloses a hemofiltration system which is based on the aforementioned apparatus with the provision that only one ultrafilter is used for sterilizing the dialysis solution. This filter must be specially monitored to enable any leak occurring to be detected immediately. This relatively complicated arrangement is eliminated in the systems mentioned above by providing two filters.

However, all the problem solutions referred to have the disadvantage that the filters always form units which are separate from each other. This means that in each case two filters are used in a cascade and must be traversed in succession. Difficulties are encountered in the regular testing of the integrity of the membranes, the complicated handling on installing the filter cascade and the resulting risk of contamination of the path between the two filters. A contamination of this space reduces the cascade automatically to one filter again. Subsequent sterilization of the overall system also encounters difficulties because due to the nonuniform flow conditions germs frequently survive in the primary filtration space. If no contamination is present in this space at the start no germs are found there later during operation either.

DE-GM No. 8,512,777 and EP-A-No. 76,421 disclose a capillary filter arrangement in which within a housing two capillary fibre bundles are arranged which are in flow connection at their ends, only one housing end being provided with the supply and discharge tubular connecting pieces. Consequently, this is only one compressed conventional hollow fibre filter so that the problems outlined above occurring when using one filter are also encountered here.

The problem underlying the invention is to further develop a capillary filter arrangement according to the preamble of claim 1 in such a manner that the liquid or solution to be filtered is subjected to two filtration steps in such a manner that by a bubble-point test (application of a pressure gradient to the space between the capillary membranes with respect to the two capillary inner spaces with the membrane wetted and air filling of the particular side subjected to the higher pressure) the integrity thereof can be tested in simple manner without germs being able to reach the space between the capillary membranes.

This problem is solved in that the two capillary fibre bundles are arranged in a tubular housing and that the ends of the housing each have a casting layer in which the ends of the capillary fibre bundles are received, and are sealed in each case with an end cap having at least one connection opening, and between the end cap and casting layer in each case a distributing chamber is formed and in the tubular housing between the cast layers a primary filtrate chamber is formed, and that the ends of the first capillary fibre bundle are sealed with respect to the first distributing chamber and the ends of the second capillary fibre bundle are sealed with respect to the second distributing chamber so that the total internal lumen of the first and second capillary fibre bundle is in flow connection only with the second and first distributing chamber respectively.

In the tubular housing of the capillary filter arrangement two semipermeable capillary fibre bundles in flow connection are arranged adjacent each other. The opposite openings of the housing are each sealed by an end cap having at least one connection opening for introduction and discharge of the medium. The housing has at its respective end a cast layer in which the ends of the capillary fibre bundles are received so that between the cast layers and the end caps first and second distributing chambers are formed. In the region of the first cast layer the capillary inner space of the first capillary fibre bundle is sealed and in the region of the second cast layer the capillary inner space of the second capillary fibre bundle is sealed. The cast layers seal the space between the capillaries of the capillary fibre bundles and the inner surface of the housing in the region near the end, and between the outer surfaces of the capillaries and the housing inner surface a primary filtrate chamber is formed. As a result the entire internal lumen of the first and second capillary fibre bundle is in flow communication only with the second and first distributing chamber respectively.

According to a preferred embodiment the housing comprises at least one outlet opening for carrying away the filtrate medium, said opening connecting the primary filtrate chamber to the exterior space.

At least one of the connecting openings advantageously comprises a tubular connecting piece preferably having a Luer lock connection, the connection piece or one of the outlet openings preferably being sealed with a hydrophobic microporous sterile filter.

Advantageously the membrane of at least one of the capillary fibre bundles may comprise adsorptive substances.

To increase the filtration effect at least one additional filtration means is present which is arranged in the primary filtrate chamber or space between the capillary fibre bundles.

Said additional filtration means preferably consists of a semipermeable hose-like substance which surrounds at least one of the capillary fibre bundles. Advantageously this additional filtration means also has adsorptive substances. These adsorptive substances comprise positively charge surface groups, preferably quaternary ammonium groups.

A capillary filter can be made by the following steps:

introduction of two spatially separate fibre bundles into a common tubular housing part, potting the end regions of the housing with a liquid sealing composition which due to its viscosity does not penetrate fully into the capillary inner space and thereafter sets, opening the capillary internal lumina by cutting off a part of the cured sealing composition blocks, sealing an end region of each of the two capillary bundles on opposite sides with a sealing agent, attaching the end caps to the housing.

Another way of making a capillary filter can be the following method steps:

introduction of two spatially separate fibre bundles into the common housing part, possibly with the aid of a partition which is provided with a plurality of openings and the end of which is anchored in each case in the potting composition, sealing of the internal lumen of an end region on opposite sides of two fibre bundles with a sealing agent, introduction of a liquid sealing composition which fills the space between the outer surface of the capillaries and the inner surface of the housing in the regions near the end and which penetrates on the respective unsealed side into the fibre inner spaces, curing of the sealing composition, opening of the capillary internal lumina on the sides opposite the initially sealed end regions by cutting off part of the cured sealing composition blocks, attachment of the end caps to the housing.

Finally, a method for making a capillary filter can be characterized by the following steps:

sealing the inner lumen in each case of one end region on opposite sides of the fibre bundles with a sealing agent, introduction of the two fibre bundles into the common housing part, the respective open capillary ends lying opposite each other, introduction of a liquid sealing composition which fills the intermediate spaces between the capillary outer surface and housing inner surface in the two regions near the ends and which on the respective unsealed side penetrates into the fibre inner spaces, curing of the sealing composition, opening of the capillary internal lumina on the sides opposite the initially sealed end regions by cutting off a part of the cured sealing composition blocks and attachment of the end caps to the housing.

The solution according to the invention makes it possible to subject the liquid to be filtered in a housing to two filtration steps, the flow direction at the first capillary membrane being from the inside to the outside and at the second from the outside to the inside.

The construction of the capillary filter according to the invention makes it possible to test the integrity of the two filtration stages by a single bubble-point test. For this purpose, firstly an excess pressure is applied by means of air through a tubular connecting piece to the primary filtration chamber with respect to both capillary inner spaces with the membrane wetted. If the surface of one of the capillary fibre bundles is torn or otherwise damaged air bubbles emerge at the outlet openings of the fibre lumina and can be detected in the liquid disposed in the distributing chamber. If however the surface of the capillary fibre bundle is not ruptured the pressure in the housing of the capillary filter is maintained for a time because the wetted capillary membrane serves as gas barrier. On the other hand the primary filtrate chamber or space can also be filled with liquid, the air being conducted through the respective distributing space to the lumen of the respective capillary fibre bundle. In this case when a membrane is ruptured the air emerges into the primary filtrate chamber.

By reducing the volume of the primary filtration chamber of the double filter compared with the cascading of two complete filters the resterilization is facilitated due to the better flow conditions.

The new solution of the problem makes it possible to prevent subsequent contamination of the primary filtration chamber on starting operation. This eliminates the growth observed in practice of germs between the two filtration stages. Another advantage is that the production costs can be drastically reduced by using a conventional filter housing.

In addition to the advantages described a third filtration stage may be used in the system without any difficulties, for example integrated between the two membrane stages in the form of a depth-type filter. Said depth-type filter can also be equipped with specific adsorption groups, for example positive surface groups such as quaternary ammonium groups as adsorbent for pyrogens.

As membranes for the two hollow fibre bundles the usual members may be employed as used in dialysis, hemofiltration or sterile filtration irrespective of whether this is for industrial or healing purposes. Membrane materials include for example cellulose derivatives, polyamide, polysulfone or the like.

Such membranes generally have an asymmetrical structure, i.e. have a filter layer which is disposed integrally on a large-pore support layer.

The pore sizes of said filter layer are selected in accordance with the intended purpose of the membranes and for sterile filtration should at the most be 0.5, in particular about 0.25 $\mu$m. The mean pore size may be between 5 to 10 nm and 0.5 $\mu$m. Due to the hydraulic properties however usually a membrane will be chosen having a mean pore size between 0.1 to 0.5, in particular about 0.25 $\mu$m.

The thickness of the membrane and the internal diameter of the hollow filament are also not in themselves critical. Thus, the thickness of the membrane may be between 10 to 100 $\mu$m, in particular about 30 to 60 $\mu$m, whilst the internal diameter of the hollow fibre is 100 to 500 $\mu$m, especially about 150 to 300 $\mu$m.

Similarly, advantageously asymmetrical hollow fibres are used of the type in which the inner side of the filament comprises the separating membrane whilst the outer side is provided with a spongy support structure.

The two capillary fibre bundles may either by the same or different in their membrane properties and size relationships, this usually being governed by the intended purpose.

Moreover, apart from the usual hydrophilic membranes hydrophobic membranes may also be used which can only be wetted with water with the aid of hydrophilation agents. Such membranes include for example polysulfone and polyamide membranes which can be rendered wettable with water for example by hydrophilic additives, such as polyvinyl pyrrolidone, worked into the membrane material.

Apart from the mass exchange membranes described above in which a mass exchange takes place in a solution gas diffusion membranes may also be used which allow only the passage of gases but not of liquids. Such membranes are advantageously the hydrophobic membranes described above. With such membranes, for example, reactors can be gasified to sterility with oxygen, the carbon dioxide forming being carried away with excess gas supplied through the other capillary fibre bundle.

The capillary fibre bundles are secured by the usual methods to both ends of a housing by casting into a potting material.

The usual curable potting compositions may be employed, for example polyurethanes, silicones, epoxy resins, reactive resins and the like.

The arrangement according to the invention is not restricted only to the use of two capillary fibre bundles within the housing. On the contrary, depending on the intended purpose three or more capillary fibre bundles may be used which are provided either for the supply or for the discharge of the various media. It is conceivable to use for the supply of gases and of liquids different capillary fibre bundles which advantageously have a separate supply chamber so that no premature mixing of said media takes place. A similar arrangement can be provided on the exit side.

As already mentioned above, the exchange elements according to the invention may be used for the hemodialysis or the hemofiltration in the sterilization of aqueous media, in particular of dialysis solutions. On the other hand, the arrangements according to the invention can also be employed for different industrial purposes in which sterility of the medium disposed in the arrangement must be maintained. This applies for example in the microbiological production of certain substances, in particular pharmaceutical compositions. Thus, bacteria or cell cultures may be supplied within this arrangement under sterile conditions both with gas and with liquid nutrients through the membranes whilst on the other side the product made by the culture can be extracted.

The present invention will be explained in detail with the aid of examples of embodiment.

Figure 2:
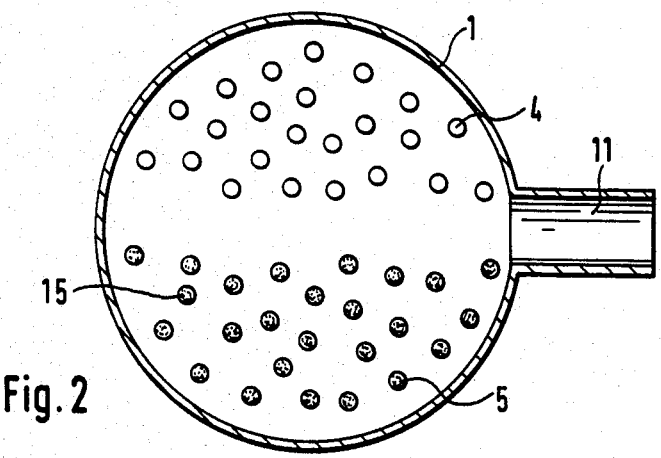
Figure 3:
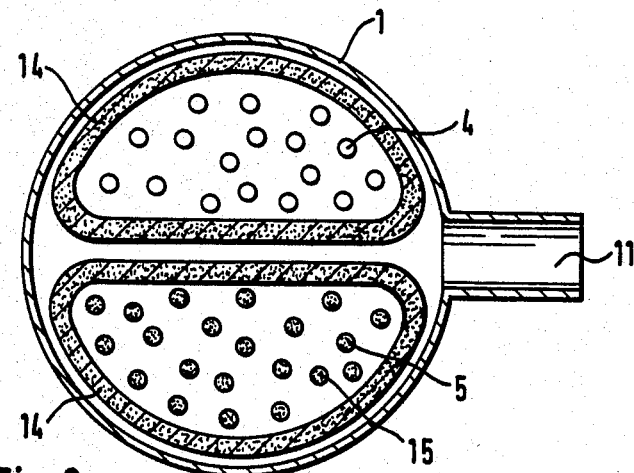

In the attached drawings:

FIG. 1 is a longitudinal section through the capillary filter according to the invention, FIG. 2 is a section at the height I—I of the capillary filter with an outlet opening offset by 90 degrees and FIG. 3 is a section at the height I—I through the capillary filter with an outlet opening offset through 90 degrees and an additional filtration means.

In accordance with FIGS. 1 and 2 the capillary filter arrangement comprises a housing body 1 consisting for example of a cylindrical tube. Two end caps 2; 2a seal the two opposite openings of said housing body 1, the end caps 2; 2a each having at least one connecting opening 3; 3a for introduction and discharge of the solution to be filtered and of the filtrate respectively.

Two capillary fibre bundles 4 and 5 are arranged adjacent each other in the tubular housing 1. The housing 1 comprises at its respective end a first and second cast layer 6; 7 in which the ends of the first and second capillary fibre bundle 4 and 5 respectively are received in such a manner that in the first and second casting layer 6 and 7 the capillary lumen of the second and first capillary fibre bundle 5 and 4 respectively is open and is in flow communication with the distributing chamber 8 and 9 respectively and in the first and second cast layer 6 and 7 the capillary lumen of the first and second capillary fibre bundle 4 and 5 respectively is sealed with a barrier layer 15; 15a. The outer faces of the capillaries and of the housing inner face form a primary filtrate chamber or space 10 between the cast layers 6 and 7. The housing 1 comprises at least one outlet opening 11 which connects the primary filtrate chamber 10 to the exterior space.

At least one of the connecting openings 3; 3a comprises a tubular connecting piece 12 with preferably Luer lock connection and a hydrophobic microporous sterile filter 13, 13a which has a mean pore size of about 0.2 $\mu$m.

On the other hand, the sterile filter 13 or 13a as shown in FIG. 1 can seal the outlet opening 11 or, as mentioned, at least one of the connecting openings 3; 3a. The essential point as regards the invention here is only that the gas necessary for the bubble-point test can be supplied to the filter under sterile conditions and that after the test only the gas and not the liquid is expelled from the filter, this being ensured by the hydrophobic properties of the sterile filter.

To increase the filtration effect at least one of the two capillary fibre bundles comprises adsorptive substances at its membrane.

The capillary filter arrangement according to FIG. 3 has at least one additional filtration means 14 which is disposed in the primary filtrate space or chamber between the capillary fibre bundles 4 and 5. Said means surrounds at least one of the capillary fibre bundles and consists preferably of a semipermeable hose-like material which may have the same separating boundary as the capillaries. Said semipermeable hose-like material is likewise anchored at its two ends in the cast layers 6 and 7 and through at least one cast layer and one end cap may be in flow communication with the surroundings by means of a supply or discharge connecting piece, not shown. This tubular connecting piece, not shown, may be constructed like the tubular connecting piece 11 and sealed with a microporous hydrophobic filter 13. This additional filtration means 14 may also advantageously contain adsorptive substances. Said adsorptive substances comprise positively charged surface groups which are preferably quaternary ammonium groups as adsorbent for pyrogens.

The capillary fibre bundles 4 and 5 consist of capillary membranes having a pore size in the range of about 0.1 . . . 0.5 $\mu$m, in particular about 0.25 $\mu$m.

The medium to be filtered is supplied for example via the connecting piece 3 to the distributing chamber 8. The medium now enters the unblocked capillary fibre bundle 5. The first filtration step now takes place, the flow direction of the incoming solution running the first capillary membrane from the inside to the outside into the primary filtrate chamber 10. In the second filtration step, which is only meant as a safety stage, the medium now moves from the outside to the inside out of the primary filtrate chamber 10 into the capillary fibre bundle 4. The filtrated liquid is now discharged via the other connecting piece or the outlet openings 11. If the medium to be filtered is supplied via the other connecting piece 3a the filtration runs in the opposite direction.

The capillary filter arrangement is sterilized, flushed, tested and vented in the manner explained below.

The basis of the test for leaks is the bubble-point test. It will be assumed that previously a dialysis has been carried out and then flushing with water or aqueous solution. When setting up the capillary fibre bundles 4 and 5 for the first time operations must be started with venting, the air being expelled by disinfectant. The capillary filter is disinfecte.,d in accordance with the disinfection program, a substitute pump pumping disinfectant into the filter at a predetermined rate, for example 200 ml per minute. Disinfectant solution is forced from the first capillary fibre bundle 5 into the second capillary filter is disinfected in accordance with the necting opening 3a. Thereafter, flushing is carried out with fresh water until it is certain that the disinfectant solution has been expelled from the entire filter by the fresh water.

Thereafter, preferably via the hydrophobic microporous sterile filter 13, air is forced into the first capillary fibre bundle 5. Since the membrane of the capillary fibre bundle 5 is wetted with water the incoming air cannot escape over the wetted filter and this makes it possible to check with the aid of the excess pressure for any cracks or holes (pinholes) which might be present in the membrane. If the filter membrane is intact a predetermined time, for example 2 minutes, is allowed to pass after reaching a transmembrane pressure of about 500 mm Hg. Thereafter the pressure at the manometer is observed and the time measured which the pressure needs to change from about 500 to 400 mm Hg. If this time is greater than about 1 minute the capillary fibre bundles 4 and 5 are considered leak-free. The capillary fibre bundle 4 is tested via the other connecting opening 3a at which a hydrophobic microporous sterile filter 13 is also disposed. If the time is less than 1 minute either one or both capillary fibre bundles have leaks.

This test can alternatively also be conducted via a sterile filter 13 arranged at an outlet opening 11, the two capillary fibre bundles 4 and 5 being tested simultaneously. If there is a leak in one of these bundles air bubbles pearl from the open ends of the capillary fibres into one of the distributing spaces or chambers 8 or 9.

After the testing stage venting is carried out, i.e. the entire system is again filled with aqueous dialysis solution, the air being expelled through the hydrophobic sterile filter 13 which then does not allow the aqueous solution to pass.

In one example of embodiment the capillary filter may be made by the following method: (shown only in the upper part of FIG. 1).

The two spatially separate capillary fibre bundles are introduced into the common housing and the end regions of the housing potted with a subsequently setting sealing composition. The capillary internal lumen is opened by cutting off part of the cured cast layer and thereafter an end region of each of the two capillary fibre bundles is sealed on the opposite sides using a setting sealing agent (e.g. polyurethane solution). Finally, the end caps are fitted in sealing manner.

In a further production method (shown only in the lower part of FIG. 1) the two spatially separate capillary fibre bundles are introduced into the common housing and the opposite end regions of the two capillary fibre bundles sealed with subsequently setting sealing composition. The end regions may however previously be sealed with the aforementioned sealing agent and then introduced into the housing.

A subsequently setting sealing composition is now introduced and fills the space between the outer surface of the capillaries and the inner surface of the housing in the regions near the end above the leve b and on the respective unsealed side penetrates into the fibre inner spaces. After the curing of the sealing composition the capillary internal lumen is opened by cutting off part of the cast layer and the end caps fitted.

The penetration level of the sealing composition is designated in FIG. 1 by a. The line (designated here by 16) of the separated part of the cast layer 7 lies between the upper level limit of a and the upper level limit of b, the severed part being shown in dashed line.

I claim:

1. Capillary filter arrangement for sterilizing liquid media comprising at least two semipermeable capillary fibre bundles which are in flow connection with each other and are arranged in a tubular housing, the ends of the housing each having a cast layer in which the capillary fibre bundles are received, the ends of the housing each being sealed with an end cap having at least one connection opening, a distributing chamber being formed between the end cap and cast layer in each case and a primary filtrate chamber being formed in the tubular housing between the cast layers, and the ends of the first capillary fibre bundle are sealed with respect to the first distributing chamber and the ends of the second fibre bundle are sealed with respect to the second distributing chamber so that the total internal lumen of the first capillary fibre bundle is in flow connection only with the second distributing chamber and that of the second capillary fibre bundle is in flow connection only with the first distributing chamber.

2. Capillary filter arrangement according to claim 1, characterized in that the housing comprises at least one outlet opening which connects the primary filtrate chamber to the exterior space.

3. Capillary filtrate arrangement according to claim 1, characterized in that at least one of the connection openings comprises a tubular connecting piece and that the tubular connecting piece or one of the outlet openings comprises a hydrophobic microporous sterile filter.

4. Capillary filter arrangement according to claim 3, characterized in that the tubular connecting piece is provided with a Luer lock connection.

5. Capillary filter arrangement according to claim 1, characterized in that the membrane of at least one of the two capillary fibre bundles includes adsorptive substances.

6. Capillary filter arrangement according to claim 1, characterized in that at least one additional filtration means is provided which is arranged in the flow direction between the capillary fibre bundles.

7. Capillary filter arrangement according to claim 6, characterized in that the additional filtration means consists of a semipermeable hose-like material which surrounds at least one of the capillary fibre bundles.

8. Capillary filter arrangement according to claim 6, characterized in that the additional filtration means contains adsorptive substances.

9. Capillary filter arrangement according to claim 8, characterized in that the adsorptive substances comprise positively charged surface groups.

10. Capillary filter arrangement according to claim 9, characterized in that the positively charged surface groups are quaternary ammonium groups.

11. Method of making a capillary filter arrangement according to claim 1, characterized in that two spatially separate capillary fibre bundles are introduced into a housing and the end region of the housing is potted with a subsequently curing sealing composition, that the capillary internal lumen of the two capillary fibre bundles is outwardly opened by severing a portion of the cured cast layer, thereafter an end region of each of the capillary fibre bundles is sealed on opposite sides with sealing composition and thereafter the end caps are attached.

12. Method according to claim 11, characterized in that the sealing composition is a liquid polyurethane composition which hardens subsequently.

13. Method of making a capillary filter arrangement according to claim 1, characterized in that the capillary fibre internal lumina of each opposite end region of the two capillary fibre bundles is sealed with a sealing composition before or after introduction of the two spatially separate capillary fibre bundles into the common housing, that a subsequently curing sealing composition is introduced which fills the space between the outer surface of the capillaries and the inner surface of the housing in the regions adjacent the ends and which on each unsealed side of the capillary fibre bundles penetrates into the fibre internal spaces, that after the curing of the sealing composition the capillary internal lumen is opened on the sides opposite the initially sealed end regions by cutting off part of the cast layer and thereafter the end caps are attached.

14. Method according to claim 13, characterized in that the sealing composition is a liquid polyurethane composition which subsequently hardens.

* * * * *